United States Patent [19]

Meffert et al.

[11] Patent Number: 4,886,893

[45] Date of Patent: Dec. 12, 1989

[54] PROCESS FOR THE PREPARATION OF MODIFIED TRIGLYCERIDES

[75] Inventors: Alfred Meffert, Monheim; Hermann Kluth, Duesseldorf, both of Fed. Rep. of Germany

[73] Assignee: Henkel Kommanditgesellschaft auf Aktien, Duesseldorf, Fed. Rep. of Germany

[21] Appl. No.: 37,126

[22] Filed: Apr. 9, 1987

Related U.S. Application Data

[63] Continuation of Ser. No. 561,627, Dec. 15, 1983, abandoned.

[30] Foreign Application Priority Data

Dec. 16, 1982 [DE] Fed. Rep. of Germany ....... 3246612

[51] Int. Cl.$^4$ ............................................ C07D 303/12
[52] U.S. Cl. ..................................... 549/562; 549/513
[58] Field of Search ............................... 549/513, 562

[56] References Cited

U.S. PATENT DOCUMENTS

| | | | |
|---|---|---|---|
| 3,042,687 | 7/1962 | Chatfield et al. | 549/562 |
| 3,051,672 | 8/1962 | Rowland et al. | 549/562 |
| 3,070,608 | 12/1962 | Kuester et al. | 549/562 |
| 3,180,749 | 4/1965 | Findley et al. | 549/562 |
| 3,242,200 | 3/1966 | Johnson | 549/562 |
| 3,699,061 | 10/1972 | Cunningham | 260/18 |

FOREIGN PATENT DOCUMENTS 1135898 12/1956 France .
132018 8/1978 German Democratic Rep. .

OTHER PUBLICATIONS

Bilyk et al., "Urethane Foams from Animal Fat:VII", Journal of the American Oil Chemist's Society, vol. 51, pp. 119-122 (1974).
Thomas W. Findley et al., in J. Am. Chem. Soc. 67, 412-414 (1945).
A. Bilyk et al., in Journal of the American Oil Chemist Society 51, 119-122 (1974).

*Primary Examiner*—Glennon H. Hollrah
*Assistant Examiner*—BA K. Trinh
*Attorney, Agent, or Firm*—Ernest G. Szoke; Wayne C. Jaeschke; Henry E. Millson, Jr.

[57] ABSTRACT

Process for the production of modified triglycerides which contain epoxide groups, secondary hydroxyl groups and ether groups. The invention particularly relates to the production of reaction products of epoxidized triglycerides, for example epoxidized soy oil, with polyfunctional alcohols, for example glycols. The products so prepared are valuable starting materials, particularly for the production of alkyd resins.

13 Claims, No Drawings

PROCESS FOR THE PREPARATION OF MODIFIED TRIGLYCERIDES

This application is a continuation, of application Ser. No. 561,627, filed 12-15-83 now abandoned.

This invention relates to organic products derived from renewable raw materials and more particularly to a process for the preparation of modified triglycerides containing epoxide groups, hydroxyl groups, and ether groups. The new modified triglycerides can be used for the production of polymers, for example, alkyd resins.

BACKGROUND OF THE INVENTION

It has long been known that naturally occurring oils and fats (triglycerides of fatty acids or fatty acid mixtures containing at least partly olefinically unsaturated double bonds) can be subjected to epoxidation which converts one or all of the double bonds in the molecule into epoxide rings. A process suitable for this purpose is described for example by Thomas W. Findley et al. in J. Am. Chem. Soc. 67, 413 (1945).

It is also known that epoxidized triglycerides, for example, epoxidized beef tallow, can be converted into higher alcohols by ring opening with polyfunctional alcohols such as trimethylol propane. A corresponding process is described by A. Bilyk et al. in Journal of the American Oil Chemist Society 51, 119 (1974).

The object of the known ring opening process is to react all the epoxide groups in the particular epoxidized triglyceride used, while accepting the fact that transesterification also occurs under the generally very rigorous reaction conditions applied.

In the course of efforts to replace petrochemical products by renewable raw materials, there was a need, particularly in the field of alkyd resins, for a raw material which contains epoxide groups as well as secondary hydroxyl groups and ether groups, and which is at least predominantly oleochemical by nature.

DESCRIPTION OF THE INVENTION

Accordingly, an object of the present invention is to provide a process for the ring opening of epoxidized triglycerides with alcohols by which it is possible to produce modified triglycerides containing epoxide groups, secondary hydroxyl groups, and ether groups (partly ring-opened epoxidized triglycerides). More particularly, an object of the invention is to provide a process for the partial ring opening of epoxidized triglycerides with $C_1$-$C_3$ alcohols. A further object of the invention is to provide modified triglycerides which contain epoxide groups, hydroxyl groups, and alkyl ether groups and which are useful for the production of improved alkyl resins.

According to the invention, the objects as stated above are achieved by the discovery of a process for partial ring opening of epoxidized triglycerides of a fatty acid mixture containing at least partly olefinically unsaturated fatty acids with monohydric or polyhydric alcohols in the presence of catalysts for the production of triglyceride reaction products which are suitable in particular for the modification of alkyd resins, wherein the reaction is terminated by destruction and/or removal of the catalyst and/or of the alcohol reactant after a conversion is achieved of from about 20 to about 80 mole percent, based on epoxide groups.

In a first embodiment of the process according to the invention, the ring opening reaction of the epoxidized triglycerides with alcohols is terminated after a conversion of from about 20 to about 80 mole percent of the epoxide groups by destruction of the catalyst. Preferred catalysts are acids, particularly mineral acids, such as sulfuric acid, phosphoric acid, hydrochloric acid, or organic acids, such as sulfonic acids, for example p-toluene sulfonic acid. The catalytic effect of the acids is eliminated by neutralization. Suitable neutralizing agents are alkali alcoholates, for example, sodium methylate.

More specifically, the process of the invention is carried out by adding a large excess of alcohol, conveniently a 2 to 10 molar excess, based on epoxide groups, to the epoxidized triglyceride. The reaction is then carried out in the presence of a small quantity of the acid catalyst at reaction temperatures in the range of from about 50 to about 110° C., and preferably at reaction temperatures in the range of from about 60° to about 80° C. The progress of the reaction can be followed from the epoxide number which can be checked by acid titration, gas chromatography or spectroscopic methods. When the epoxide number has fallen to the required predetermined value, the neutralizing agent is added. Thereafter, the excess alcohol can be removed, if desired, by distillation.

In another embodiment of the invention, heterogeneous catalysts are used. Suitable heterogeneous catalysts are, for example, ion exchange resins, i.e. strongly acidic ion exchange resins or strongly basic ion exchange resins. After the required residual epoxide number has been reached, the ion exchange resins are separated off from the reaction mixture by filtration.

In another variant of the process according to the invention, a reactant, preferably the generally more readily volatile alcohol, is removed instead of the catalyst. In this embodiment of the process, it is preferred to cool the reaction mixture to room temperature or below at the end of the desired reaction time and to remove the alcohol by distillation. Where this procedure is adopted, the catalyst remains in the reaction mixture and can therefore be subsequently used for further reactions.

As stated above, an object of the process according to the invention is t produce modified triglycerides which, in addition to epoxide groups, also contain secondary hydroxyl groups and alkyl ether groups. In one preferred embodiment, the objective is to obtain at least the greater part, i.e. more than 50%, preferably more than 70% and, in particular, more than 90% of the triglyceride skeleton. In order to avoid transesterification, it is preferred to use reaction temperatures in the range of from about 50° to about 110° C. and, more particularly, reaction temperatures in the range of from about 60° to about 80° C. Where alcohols boiling below 80° C. are used for ring opening, the reaction can be carried out at the boiling point of the particular alcohol used.

The process according to the invention is preferably carried out with alcohols having a functionality of from 1 to 4, more particularly, from 1 to 3; short-chain alcohols being more reactive than long-chain alcohols. Thus, in one special embodiment, monofunctional alcohols containing from 1 to 8 carbon atoms can be employed. It is preferred to use short-chain monofunctional alcohols, i.e. those containing up to 3 carbon atoms, such as methanol, ethanol, propanol, isopropanol or allyl alcohol. Other suitable alcohols are branched chain alcohols, such as isobutanol or neopentyl alcohol, or cyclic alcohols, such as cyclohexanol or benzyl alcohol.

In another embodiment of the invention, bifunctional alcohols preferably containing from 2 to 6 carbon atoms, and more preferably from 2 to 4 carbon atoms, are used for the ring opening reaction. In this embodiment, it is preferred to carry out the reaction in an excess of bifunctional alcohol of more than 2 moles and preferably in an excess of from 4 to 8 moles, based on the epoxide groups to be opened. This prevents products of relatively high molecular weight from being formed to any significant extent through the reaction of each of the 2 hydroxyl groups of the bifunctional alcohol with 1 molecule of epoxidized triglyceride. Suitable bifunctional alcohols are, in particular, ethylene glycol and propylene glycol, although the isomeric butane diols, pentane diols or hexane diols can also be used herein. Where these bifunctional hydroxy compounds are used for the ring opening reaction, modified triglycerides are formed which, in addition to epoxide groups, ether groups and secondary hydroxyl groups, also contain primary hydroxyl groups. The greater reactivity of primary hydroxyl groups is useful for many applications, for example, for the production of alkyd resins.

An additional ether group in the molecule can be advantageous for certain applications. To achieve this, the ring opening reaction is carried out with the monoethers of bifunctional alcohols. Suitable monoethers of bifunctional alcohols contain for example a total of from 3 to 8 carbon atoms and preferably from 3 to 5 carbon atoms. Thus, there can be used herein ethylene glycol monomethylether, monoethylether and monopropylether and also diethylene glycol or ethers of diethylene glycol as well as the corresponding compounds derived from propylene glycol.

Finally, another embodiment of the invention relates to the partial ring opening of epoxidized triglycerides by trifunctional alcohols containing from 3 to 6 carbon atoms, preferably glycerol or trimethylol propane. Since these alcohols are substantially nonvolatile, excess alcohols of this type are removed in a high vacuum, for example in a thin layer evaporator, on completion of the reaction. Through the use of trifunctional alcohols for the ring opening reaction, modified triglycerides are formed which, in addition to epoxide groups and ether groups, contain numerous hydroxyl groups. The greater degree of hydrophilicity which results therefrom is desirable for numerous applications.

The process according to the invention can be carried out with a number of epoxidized triglycerides of vegetable or animal origin. The only requirement is that a substantial percentage of epoxide groups should be present. Thus, suitable epoxidized triglycerides are for example those containing from about 2 to about 10% by weight of epoxide oxygen. Products containing from about 4 to about 8.5% by weight of epoxide oxygen are particularly suitable. They can be produced from the following fats and oils (in order of their starting iodine number): beef tallow, palm oil, lard, castor oil, peanut oil, rape oil and, preferably, cottonseed oil, soybean oil, train oil, sunflower oil, and linseed oil. Particularly preferred starting materials are epoxidized soybean oil having an epoxide number of from 5.8 to 6.5, epoxidized sunflower oil having an epoxide number of from 5.6 to 6.6, epoxidized linseed oil having an epoxide number of from 8.2 to 8.6 and epoxidized train oil having an epoxide number of from 6.3 to 6.7.

It is possible by using the process of the invention to produce modified triglycerides which have a high residual content of hydroxyl and alkyl ether groups (20%). However, it is also possible to obtain products which have a low content of residual epoxide groups (20%) and a high content of hydroxyl and alkyl ether groups (80%) and also any intermediate values. For numerous applications, it is desirable that the number of epoxide groups be substantially equal to the number of hydroxyl and alkyl ether groups. Accordingly, it is preferred to subject from about 30 to about 70 mole percent of the epoxide groups and, more particularly, from about 40 to about 60 mole percent of the epoxide groups to the ring opening reaction.

The products prepared in accordance with the process of the invention are suitable for use as starting materials for the production of polymers, particularly alkyd resins. They can be incorporated in alkyd resins by condensation, both through their epoxide groups and through their hydroxyl groups and, accordingly, provide new, natural polyfunctional starting materials for polycondensation reactions.

U.S. application Ser. No. 561,626, now U.S. Pat. No. 4,474,941 filed of even date herewith, discloses a method for the use of the present products as starting materials for the preparation of alkyd resins, and the disclosures of the above copending application are specifically incorporated herein by reference. The process of this copending application is carried out, generally in the presence of an acid catalyst such as p-toluene sulfonic acid, at a temperature of about 200° C. by condensing polybasic carboxylic acids such as adipic acid or their reactive derivatives with polyhydroxy compounds such as ethylene glycol and cocondensing therewith a long-chain alkyd resin modifying reaction component which can be a product prepared by the process of the present invention.

The invention will be illustrated by the following examples, which are given for that purpose only, and not for purposes of limitation.

EXAMPLE 1

1050 g of epoxidized soy oil (6.1% by weight of epoxide oxygen) were heated to reflux temperature with 385 g of methanol and 4 g of concentrated sulfuric acid, followed by stirring for 90 minutes at that temperature. 7.3 g of a 30% sodium methylate solution in methanol were then added, after which excess methanol was removed <first at normal pressure and then in vacuo. A modified soy triglyceride containing epoxide groups, hydroxyl, and methyl ether groups was formed. It had a residual epoxide content of 3.26% by weight of epoxide oxygen.

EXAMPLE 2

250 g of ethylene glycol and 1.2 g of concentrated sulfuric acid were heated to 90° C. in a standard reaction vessel. 1050 g of epoxidized soy oil (6.1% by weight of epoxide oxygen) were added over a period of 20 minutes, while ensuring that the temperature did not exceed 100° C. After 30 minutes, the reaction was terminated by the addition of 3.8 g of a 30% solution of sodium methylate in methanol. Excess ethylene glycol was distilled off in vacuo (approximately $10^{-5}$ bars). The product formed had a residual epoxide content of 2.5% by weight of epoxide oxygen.

EXAMPLE 3

96 g of methanol and 0.5 g of concentrated sulfuric acid were heated to the boiling point in a standard reaction vessel. 125 g of epoxidized sunflower oil (6.4% by weight of epoxide oxygen) were then added over a period of 30 minutes, followed by heating under reflux (of the boiling methanol) for 4 hours. 0.7 g of a 30% sodium methylate solution in methanol were then added and excess methanol distilled off. The product formed contained 3.6% by weight of epoxide oxygen.

EXAMPLE 4

128 g of methanol and 2 g of concentrated sulfuric acid were heated to boiling temperature in a standard apparatus, followed by the addition over a period of 25 minutes of 380 g of epoxidized linseed oil (8.45% by weight of epoxide oxygen). The mixture was then kept boiling under reflux (of the methanol) for 30 minutes, after which the reaction was terminated by the addition of 3.1 g of a 30% by weight sodium methylate solution in methanol. Removal of the excess methanol by distillation left a product containing 3.5% by weight of epoxide oxygen.

EXAMPLE 5

96 g of methanol and 0.5 g of sulfuric acid were heated to boiling temperature in a standard reaction vessel, followed by the addition of 123 g of train oil epoxide (6.5% by weight of epoxide oxygen). The reaction mixture was then left standing for 6 hours at that temperature. Thereafter the catalyst was neutralized by the addition of 0.7 g of a 30% by weight solution of sodium methylate in methanol. Removal of the excess methanol by distillation left a product having a residual epoxide content of 3.87% of epoxide oxygen.

EXAMPLE 6

To determine the degree of transesterification that occurred, the procedure described in EXAMPLE 1 was repeated. In this example, however, the ring opening reaction was not terminated, but instead was continued until a complete conversion had been obtained (after about 6 hours). Analysis by gas chromatography revealed a content of approximately 2 to 3% by weight of modified fatty acid methyl esters together with another 5% by weight of volatile constituents.

What is claimed is:

1. A process for the partial ring opening of epoxidized triglycerides of a fatty acid mixture wherein the fatty acid mixture contains at least partly olefinically unsaturated fatty acids comprising the step of
   (A) reacting said epoxidized triglycerides with a large excess, based on epoxide groups, of at least one alcohol in the presence of a small quantity of an acidic or a strongly basic catalyst at a temperature in the range of from about 50° to about 110° C.; and
   (B) terminating the reaction after from about 30 to about 70 mole percent of the epoxide groups in the epoxidized triglycerides are opened;
   wherein the alcohol reactant in step (A) is one or more of the following:
   (i) a primary or secondary, saturated or unsaturated monofunctional alcohol containing from 1 to 8 carbon atoms,
   (ii) a bifunctional alcohol containing from 2 to 6 carbon atoms,
   (iii) a monoether of a bifunctional alcohol containing a total of from 3 to 8 carbon atoms, and
   (iv) a trifunctional alcohol containing from 3 to 6 carbon atoms; and
   wherein the epoxidized triglyceride in step A contains from about 5.6 to about 10% by weight of epoxide oxygen.

2. A process in accordance with claim 1 wherein the alcohol in (i) contains from 1 to 3 carbon atoms, the bifunctional alcohol in (ii) contains from 2 to 4 carbon atoms, and the monoether in (iii) contains from 3 to 5 carbon atoms.

3. A process in accordance with claim 1 wherein the acid catalyst is sulfuric acid, phosphoric acid, or a sulfonic acid.

4. A process in accordance with claim 1 wherein the alcohol reactant in step (A) is present in a 2 to 10 molar excess, based on the epoxide groups present in the epoxidized triglycerides.

5. A process in accordance with claim 1 wherein the temperature is in the range of from about 60 to about 80° C.

6. A process in accordance with claim 1 wherein in step (B) the reaction is terminated after from about 40 to about 60 mole percent of the epoxide groups are opened.

7. A modified triglyceride containing epoxide groups, hydroxyl groups and alkyl ether groups produced by the process of claim 1.

8. A modified triglyceride containing epoxide groups, hydroxyl groups and alkyl ether groups produced by the process of claim 2.

9. A modified triglyceride containing epoxide groups, hydroxyl groups and alkyl ether groups produced by the process of claim 4.

10. The process of claim 1 wherein in step B the reaction is terminated by destruction of the catalyst.

11. The process of claim 1 wherein in step B the reaction is terminated by removal of the catalyst.

12. The process of claim 1 wherein in step B the reaction is terminated by removal of unreacted alcohol.

13. The process of claim 1 wherein the epoxidized triglyceride in step A is at least one of epoxidized soybean oil having an epoxide number of from about 5.8 to about 6.5, epoxidized sunflower oil having an epoxide number of from about 5.6 to about 6.6, epoxidized linseed oil having an epoxide number of from about 8.2 to about 8.6, and epoxidized train oil having an epoxide number of from about 6.3 to about 6.7.

* * * * *